US012569377B2

(12) United States Patent (10) Patent No.: US 12,569,377 B2
Blomström et al. (45) Date of Patent: Mar. 10, 2026

(54) ABSORBENT ARTICLE

(71) Applicant: Essity Hygiene and Health Aktiebolag, Gothenburg (SE)

(72) Inventors: Philip Blomström, Gothenburg (SE); Shabira Abbas, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 726 days.

(21) Appl. No.: 17/429,508

(22) PCT Filed: Feb. 15, 2019

(86) PCT No.: PCT/SE2019/050130
    § 371 (c)(1),
    (2) Date: Aug. 9, 2021

(87) PCT Pub. No.: WO2020/167171
    PCT Pub. Date: Aug. 20, 2020

(65) Prior Publication Data
    US 2022/0047433 A1      Feb. 17, 2022

(51) Int. Cl.
    *A61F 13/511*      (2006.01)
    *A61F 13/15*      (2006.01)
    (Continued)

(52) U.S. Cl.
    CPC ...... *A61F 13/51108* (2013.01); *A61F 13/513* (2013.01); *A61F 13/537* (2013.01);
    (Continued)

(58) Field of Classification Search
    CPC ...... A61F 13/51104; A61F 2013/15365; A61F 2013/15406; A61F 2013/15447;
    (Continued)

(56) References Cited

U.S. PATENT DOCUMENTS 3,315,677 A 4/1967 Tyrrell, Jr.
3,512,530 A 5/1970 Jones
(Continued)

FOREIGN PATENT DOCUMENTS

AU 2015412559 B2 2/2019
CN 1363258 A 8/2002
(Continued)

OTHER PUBLICATIONS

Office Action (Examination Report No. 1) issued on Oct. 15, 2021, by the Australian Patent Office in corresponding Australian Patent Application No. 2019429634. (3 pages).
(Continued)

*Primary Examiner* — Jessica Arble
(74) *Attorney, Agent, or Firm* — BUCHANAN INGERSOLL & ROONEY PC

(57) ABSTRACT

The absorbent article as disclosed herein has longitudinal side edges extending in a longitudinal direction and transverse front and rear end edges extending in a transverse direction. The absorbent article comprises a fluid permeable surface layer, a backsheet and an intermediate layer located between the fluid permeable surface layer and the backsheet. The surface layer has a wearer-facing portion facing the user during use. The surface layer is an air through bonded fibrous nonwoven surface layer having a basis weight of from 14 to 30 g/m2 and a density of from 20 to 90 kg/m3. The intermediate layer extends under from 70 to 100% of the wearer-facing portion of the surface layer. The intermediate layer and the surface layer have a respective elongation at 10 N/50 mm. The elongation of the intermediate layer is lower than the elongation of the surface layer.

16 Claims, 3 Drawing Sheets

(51) Int. Cl.
    *A61F 13/513*      (2006.01)
    *A61F 13/537*      (2006.01)
    *A61F 13/539*      (2006.01)
(52) U.S. Cl.
    CPC .. *A61F 13/539* (2013.01); *A61F 2013/15869*
        (2013.01); *A61F 2013/15878* (2013.01); *A61F*
            *2013/1591* (2013.01); *A61F 2013/51178*
                                            (2013.01)
(58) Field of Classification Search
    CPC .. A61F 2013/51078; A61F 2013/51083; A61F
                                            2013/51139
    See application file for complete search history.

(56)                References Cited

U.S. PATENT DOCUMENTS

|              |       |         |                          |
|--------------|-------|---------|--------------------------|
| 3,595,237    | A     | 7/1971  | Sargent et al.           |
| 3,643,662    | A     | 2/1972  | McGuire et al.           |
| 4,690,680    | A     | 9/1987  | Higgins                  |
| 5,009,651    | A     | 4/1991  | Kamishioiri et al.       |
| 5,069,677    | A     | 12/1991 | Sakurai et al.           |
| 5,078,710    | A     | 1/1992  | Suda et al.              |
| 5,119,257    | A     | 6/1992  | Itou et al.              |
| 6,187,699    | B1    | 2/2001  | Terakawa et al.          |
| 6,617,490    | B1    | 9/2003  | Chen et al.              |
| 7,267,860    | B2    | 9/2007  | Toyoshima et al.         |
| 7,628,777    | B2    | 12/2009 | Kondo et al.             |
| 8,658,852    | B2    | 2/2014  | Paldey                   |
| 9,173,786    | B2    | 11/2015 | Roh et al.               |
| 9,198,808    | B2    | 12/2015 | Yoshioka et al.          |
| 9,205,006    | B2    | 12/2015 | Cheng et al.             |
| 9,566,761    | B2    | 2/2017  | Mitsuno et al.           |
| 9,622,921    | B2    | 4/2017  | Kudo et al.              |
| 10,307,304   | B2    | 6/2019  | Kurihara                 |
| 11,033,441   | B2    | 6/2021  | Xu et al.                |
| 11,214,902   | B2    | 1/2022  | Bogren et al.            |
| 2002/0029024 | A1    | 3/2002  | Furuya et al.            |
| 2002/0143312 | A1*   | 10/2002 | Graeme, III ...... A61F 13/51104 |
|              |       |         |                   604/385.01 |
| 2003/0018314 | A1    | 1/2003  | Nozaki et al.            |
| 2003/0088231 | A1    | 5/2003  | Yoshimasa et al.         |
| 2003/0163109 | A1    | 8/2003  | Ohba et al.              |
| 2003/0187417 | A1    | 10/2003 | Kudo et al.              |
| 2004/0254552 | A1    | 12/2004 | Mangold                  |
| 2004/0267220 | A1    | 12/2004 | Hull et al.              |
| 2005/0041312 | A1    | 2/2005  | Sommer                   |
| 2005/0148970 | A1    | 7/2005  | Kudo et al.              |
| 2005/0148971 | A1    | 7/2005  | Kuroda et al.            |
| 2006/0116652 | A1    | 6/2006  | Miura et al.             |
| 2006/0142724 | A1    | 6/2006  | Watanabe et al.          |
| 2006/0271008 | A1    | 11/2006 | Tanio et al.             |
| 2007/0043330 | A1    | 2/2007  | Lankhof et al.           |
| 2007/0073253 | A1    | 3/2007  | Miyama et al.            |
| 2008/0319411 | A1    | 12/2008 | Mortensen et al.         |
| 2010/0035014 | A1    | 2/2010  | Hammons et al.           |
| 2011/0106036 | A1    | 5/2011  | Staahl et al.            |
| 2011/0125120 | A1    | 5/2011  | Nishitani et al.         |
| 2012/0103504 | A1    | 5/2012  | Deng et al.              |
| 2012/0165776 | A1    | 6/2012  | McGregor et al.          |
| 2012/0238984 | A1    | 9/2012  | Paldey                   |
| 2013/0245589 | A1*   | 9/2013  | Toda ............... A61F 13/53747 |
|              |       |         |                   604/378 |
| 2014/0066873 | A1    | 3/2014  | Kawakami et al.          |
| 2014/0163507 | A1*   | 6/2014  | Kudo ............... A61F 13/51104 |
|              |       |         |                   604/385.01 |
| 2014/0276512 | A1    | 9/2014  | Cheng et al.             |
| 2014/0343525 | A1    | 11/2014 | Roh et al.               |
| 2015/0051566 | A1    | 2/2015  | Noda et al.              |
| 2015/0164709 | A1    | 6/2015  | Mcgregor et al.          |
| 2015/0182387 | A1    | 7/2015  | Ferrer et al.            |
| 2015/0320616 | A1*   | 11/2015 | Schmitz ............... A61F 13/495 |
|              |       |         |                   604/380 |
| 2015/0366726 | A1    | 12/2015 | Noda et al.              |
| 2016/0089277 | A1    | 3/2016  | Barbosa et al.           |
| 2016/0220421 | A1    | 8/2016  | Kuramochi                |
| 2016/0270973 | A1    | 9/2016  | Surushe et al.           |
| 2017/0065460 | A1*   | 3/2017  | Rosati ................. A61F 13/539 |
| 2017/0143559 | A1    | 5/2017  | Kurihara                 |
| 2017/0172818 | A1    | 6/2017  | Suzuki                   |
| 2017/0239101 | A1    | 8/2017  | Lee et al.               |
| 2018/0028372 | A1    | 2/2018  | Fernkvist et al.         |
| 2018/0214318 | A1    | 8/2018  | Ashraf et al.            |
| 2018/0303680 | A1    | 10/2018 | Hood et al.              |
| 2022/0047433 | A1    | 2/2022  | Blomström et al.         |
| 2022/0087879 | A1    | 3/2022  | Blomström et al.         |
| 2022/0096282 | A1    | 3/2022  | Blomström et al.         |

FOREIGN PATENT DOCUMENTS

|    |               |    |         |
|----|---------------|----|---------|
| CN | 1406566       | A  | 4/2003  |
| CN | 1448118       | A  | 10/2003 |
| CN | 1625377       | A  | 6/2005  |
| CN | 1679455       | A  | 10/2005 |
| CN | 101090689     | A  | 12/2007 |
| CN | 101325939     | A  | 12/2008 |
| CN | 102257199     | A  | 11/2011 |
| CN | 103140201     | A  | 6/2013  |
| CN | 103429209     | A  | 12/2013 |
| CN | 104955428     | A  | 9/2015  |
| CN | 204798134     | U  | 11/2015 |
| CN | 105167915     | A  | 12/2015 |
| CN | 106572929     | A  | 4/2017  |
| CN | 107106381     | A  | 8/2017  |
| CN | 108430417     | A  | 8/2018  |
| CN | 108431316     | A  | 8/2018  |
| CO | 08072557      |    | 7/2008  |
| CO | 20210008560   | A2 | 7/2021  |
| DE | 3145398       | A1 | 9/1982  |
| DE | 69215465      | T3 | 10/2002 |
| DE | 10144128      | A1 | 3/2003  |
| DE | 60019856      | T2 | 6/2005  |
| DE | 60312404      | T2 | 11/2007 |
| DE | 102015010105  | A1 | 2/2017  |
| EP | 0025315       | A1 | 3/1981  |
| EP | 0171806       | A2 | 2/1986  |
| EP | 0359501       | A2 | 3/1990  |
| EP | 0532005       | A1 | 3/1993  |
| EP | 0705585       | A1 | 4/1996  |
| EP | 0923921       | A1 | 6/1999  |
| EP | 1077053       | A2 | 2/2001  |
| EP | 1181917       | A2 | 2/2002  |
| EP | 1035818       | B1 | 4/2002  |
| EP | 1290995       | A2 | 3/2003  |
| EP | 1329207       | A2 | 7/2003  |
| EP | 1348413       | A1 | 10/2003 |
| EP | 1338262       | B1 | 10/2005 |
| EP | 1990033       | A1 | 11/2008 |
| EP | 2011463       | A2 | 1/2009  |
| EP | 1290995       | B1 | 8/2009  |
| EP | 3001992       | A1 | 4/2016  |
| EP | 1077052       | B2 | 11/2016 |
| EP | 3238680       | A1 | 11/2017 |
| GB | 2087730       | A  | 6/1982  |
| GB | 2304586       | A  | 3/1997  |
| GB | 2358588       | A  | 8/2001  |
| JP | H0453554      | A  | 2/1992  |
| JP | 2765910       | B2 | 6/1998  |
| JP | 4146192       | B2 | 6/2008  |
| JP | 4359020       | B2 | 8/2009  |
| JP | 4851169       | B2 | 10/2011 |
| JP | 2011234896    | A  | 11/2011 |
| JP | 5938438       | B2 | 6/2016  |
| JP | 2017029494    | A  | 2/2017  |
| JP | 6219573       | B2 | 10/2017 |
| RU | 24771         | U1 | 8/2002  |
| RU | 2625931       | C2 | 7/2017  |
| WO | 9610975       | A1 | 4/1996  |
| WO | 9629968       | A1 | 10/1996 |
| WO | 0112118       | A1 | 2/2001  |
| WO | 2010074208    | A1 | 7/2010  |
| WO | 2011155284    | A1 | 12/2011 |
| WO | 2012176656    | A1 | 12/2012 |
| WO | 2016002351    | A1 | 1/2016  |

(56) References Cited

FOREIGN PATENT DOCUMENTS

| WO | 2016032488 | A1 | 3/2016 |
| WO | 2017186935 | A1 | 11/2017 |
| WO | 2018020688 | A1 | 2/2018 |
| WO | 2018226131 | A1 | 12/2018 |
| WO | 2020167171 | A1 | 8/2020 |

OTHER PUBLICATIONS

Office Action issued on Jul. 31, 2023, in corresponding Colombian Patent Application No. NC2021/0010210. (7 pages).

Search Report/Written Opinion issued on Aug. 3, 2023, in corresponding Brazilian Patent Application No. BR112021012893-0. (4 pages).

Notification of the Third Office Action issued on Jan. 9, 2023, by the Chinese Patent Office in Chinese Patent Application No. 201980087891.X and English Translation of the Office Action. (13 pages).

Office Action issued on Jul. 24, 2023, in Colombian Patent Application No. NC2021/0008560. (10 pages).

Office Action issued on Mar. 27, 2023, in Colombian Patent Application No. NC2021/0008560 and partial English translation. (9 pages).

Search Report/Written Opinion issued on Aug. 3, 2023, in Brazilian Patent Application No. BR112021012886-7. (4 pages).

Third Party Observation dated May 23, 2023, in Brazilian Patent Application No. BR112021013947-8. (13 pages).

Office Action (Communication pursuant to Article 94(3) EPC) issued on Sep. 22, 2023, in corresponding European Patent Application No. 19915083.0. (4 pages).

Second Office Action dated Aug. 5, 2022, Issued in the corresponding Chinese Patent Application No. 201980087891.X, 16 pages including 8 pages of English Translation.

Extended European Search Report dated Aug. 5, 2022, issued in the corresponding European Patent Application No. 19914736.4, 7 pages.

Office Action (Decision of Rejection) issued on Jun. 29, 2022, by the Chinese Patent Office in corresponding Chinese Patent Application No. 201980088038.X, and an English Translation of the Office Action. (10 pages).

Office Action (Notification of the Second Office Action) issued on Aug. 5, 2022, by the Chinese Patent Office in corresponding Chinese Patent Application No. 201980087891.X, and an English Translation of the Office Action. (16 pages).

The extended European Search Report issued on Aug. 5, 2022, by the European Patent Office in corresponding European Application No. 19914736.4. (7 pages).

The extended European Search Report issued on Aug. 5, 2022, by the European Patent Office in corresponding European Application No. 19915083.0. (9 pages).

The extended European Search Report issued on Aug. 11, 2022, by the European Patent Office in corresponding European Application No. 19915027.7. (7 pages).

Office Action issued in U.S. Appl. No. 17/429,549, dated Feb. 1, 2024, 12 pages.

Examination Report No. 1 dated Nov. 22, 2021, issued in the Australian Patent Application No. 2019429116, 4 pages.

Office Action dated Jan. 11, 2022, issued in the Chinese Patent Application No. 201980087891.X, 17 pages including 8 pages of English Translation.

First Office Action dated Dec. 24, 2021, issued in the Chinese Patent Application No. 201980088037.5, with English Translation, 16 pages.

Office Action dated Dec. 16, 2021, issued in the Chinese Patent Application No. 201980088038.X, 16 pages including 8 pages of English Translation.

Third Party Observation dated Dec. 14, 2021, issued in the Mexican Patent Application No. MX/a/2021/009824, with English Translation, 16 pages.

Third Party Observation dated Dec. 14, 2021, issued in the Mexican

Patent Application No. MX/a/2021/009794, 16 pages.

Third Party Observation dated Dec. 14, 2021, issued in the Mexican Patent Application No. MX/a/2021/009801, 15 pages.

Opposition Filed on Jan. 14, 2022 in Colombian Patent Application No. NC2021/0008560, 22 pages.

Office Action dated Dec. 21, 2021, issued in the Russian Patent Application No. 2021122138, 13 pages and English Translation.

Office Action dated Dec. 23, 2021, issued in the Russian Patent Application No. 2021122381, 13 pages and English Translation.

Examination Report No. 1 dated Oct. 21, 2021, issued in the Australian Patent Application No. 2019429674, 4 pages.

Opposition Filed on Aug. 9, 2021 in Colombian Patent Application No. NC2021/0010210, 18 pages.

Opposition Filed on Mar. 1, 2022 in Colombian Patent Application No. NC2021/0009675, 22 pages.

Office Action dated Sep. 14, 2022 issued in corresponding Chinese Patent Application No. 201980088037.5, 13 pages including 8 pages of English Translation.

Office Action issued on Oct. 20, 2023, in Colombian Patent Application No. NC2021/0009675 and partial English summary. (12 pages).

International Search Report (PCT/ISA/210) and Written Opinion (PCT/ISA/237) mailed on Nov. 1, 2019, by the Swedish Patent Office as the International Searching Authority for International Application No. PCT/SE2019/050130.

International Search Report (PCT/ISA/210) and Written Opinion (PCT/ISA/237) mailed on Nov. 1, 2019, by the Swedish Patent Office as the International Searching Authority for International Application No. PCT/SE2019/050131.

International Search Report (PCT/ISA/210) and Written Opinion (PCT/ISA/237) mailed on Oct. 16, 2019, by the Swedish Patent Office as the International Searching Authority for International Application No. PCT/SE2019/050132.

Office Action issued on Jun. 11, 2024, by the U.S. Patent and Trademark Office in U.S. Appl. No. 17/429,511. (18 pages).

Office Action issued on Dec. 28, 2023, in Colombian Patent Application No. NC2021/0008560. (8 pages).

Office Action issued by the U.S. Patent and Trademark Office in the U.S. Appl. No. 17/429,511, mailed Feb. 28, 2024, U.S. Patent and Trademark Office, Alexandria, VA. (71 pages).

Office Action issued on Dec. 29, 2023, in corresponding Colombian Patent Application No. NC2021/0010210. (8 pages).

Office Action issued on Jul. 5, 2024, by the Colombian Patent Office in corresponding Colombian Patent Application No. NC2021/0010210, and a machine English Translation of the Office Action. (19 pages).

Office Action issued on Sep. 3, 2024, by the U.S. Patent and Trademark Office in U.S. Appl. No. 17/429,549. (34 pages).

Office Action issued on Oct. 15, 2024, by the U.S. Patent and Trademark Office in co-pending U.S. Appl. No. 17/429,511. (22 pages).

Office Action (Final Rejection) issued on Mar. 5, 2025, by the U.S. Patent and Trademark Office in co-pending U.S. Appl. No. 17/429,549. (18 pages).

"Test Methods for Nonwovens", Part 2: Determination of Thickness, Second Edition, International Standard, ISO 9073-2:1995(E), Mar. 15, 1995. (9 pages).

Affidavit for submission to the European Patent Office by Krzysztof-Daniel Malowaniec dated Dec. 18, 2024, with machine English Translation. (4 pages).

Affidavit for submission to the European Patent Office by Tamara Buch dated Dec. 21, 2024, with machine English Translation. (6 pages).

Hartmann, "Analysis Report", Order No. 2400865, Dec. 20, 2024, with machine English Translation. (50 pages).

Hartmann, "Analysis Report", Order No. 1401053, Dec. 12, 2014, with machine English Translation. (6 pages).

Hartmann, "Analysis Report", Order No. 1401052, Jan. 15, 2015, with machine English Translation. (6 pages).

Domininghaus, "Plastics and Their Properties", 5th Edition, VDI, 1998. (6 pages).

(56)         References Cited

OTHER PUBLICATIONS

Dtex Calculation of the Topsheet Fibers from the Japanese reference sample Unicharm (LA 2400865), with machine English Translation. (2 pages).

Dtex Calculation of Topsheet Fibers of Japanese Reset Pattern (LA 24007400), KAO Topsheet, with English Translation. (2 pages).

Email correspondence to Satomi Ishibashi from Chris Malowaniec dated May 22, 2014 to Jun. 8, 2014. (12 pages).

GWP, "Optical Roughness Measurement", Report 28488-02, Nov. 5, 2024. with English Translation. (32 pages).

Hartmann, "Analysis Report", Order No. 2400740, Dec. 20, 2024, with English Translation. (44 pages).

Invoices, Mr. Nobuaki Kawai, Unicharm Corporation, Jun. 2, 2014. (8 pages).

IR Spectrum, Unicharm Topsheet. (1 page).

IR Spectrum, KAO Topsheet. (1 page).

Microscope Image from Laboratory Report 2400740, KAO Topsheet, Oct. 21, 2024, with machine English Translation. (2 pages).

Office Action (Communication of a Notice of Opposition) issued on Jan. 16, 2025, by the European Patent Office in corresponding European Patent Application No. 19914736.4. (20 pages).

Office Action (Communication of a Notice of Opposition) issued on Jan. 10, 2025, by the European Patent Office in corresponding European Patent Application No. 19914736.4. (35 pages).

Office Action (Notice of Opposition to a European Patent) issued on Jan. 3, 2025, by the European Patent Office in corresponding European Patent Application No. 19914736.4. (27 pages).

Office Action issued on Jul. 6, 2021, by the Egyptian Patent Office in corresponding Egyptian Patent Application No. EG/P/2021/01047, and a partial English Translation of the Office Action. (7 pages).

GWP, "Optical Roughness Measurement", Report 28488-03, Nov. 5, 2024, with machine English Translation. (84 pages).

Microscope Image from Laboratory Report 2400865, Unicharm Topsheet, Oct. 21, 2024, with machine English Translation. (2 pages).

Office Action issued on May 27, 2025, by the U.S. Patent and Trademark Office in co-pending U.S. Appl. No. 17/429,511. (24 pages).

Office Action (Notification of Reexamination) issued on Aug. 20, 2025, by the Chinese Patent Office in corresponding Chinese Patent Application No. 201980088038.X, and an English Translation of the Office Action. (20 pages).

Office Action issued on Aug. 23, 2025, by the Egyptian Patent Office in corresponding Egyptian Patent Application No. EG/P/2021/01048, and an English Translation. (7 pages).

Office Action issued on Sep. 17, 2025, by the U.S. Patent and Trademark Office in co-pending U.S. Appl. No. 17/429,511. (22 pages).

Office Action issued on Dec. 1, 2025, by the U.S. Patent and Trademark Office in co-pending U.S. Appl. No. 17/429,511. (23 pages).

Communication of a Notice of Opposition dated Jan. 9, 2026, issued in the corresponding European Patent Application No. EP 19915083. 0, including two (2) Notice of Oppositions filed on Dec. 23, 2025, and Jan. 2, 2026. (46 pages).

* cited by examiner

*Friction (gmf)*

800

700

600

500

400

300

200

100

0

*Number of runs*

- - - - CEx1     —— test sample     - · - CEx2

ABSORBENT ARTICLE

TECHNICAL FIELD

The present invention relates to an absorbent article. The present invention in particular relates to an absorbent article having a low-friction surface layer.

BACKGROUND OF THE INVENTION

Absorbent articles of the kind to which this disclosure relates are worn against the skin and include a topsheet, an absorbent core and a backsheet layer. All uses of products which are applied in direct contact with the skin may lead to unwanted side-effects. These may occur as a result of occlusion, moisture and mechanical factors, such as friction, between the skin and the absorbent article. These factors which all, to different degrees, interact and amplify the influence of each other and may cause different forms of skin irritation to users of said articles. Skin problems can be caused by forces arising from physical/mechanical interaction between the product and the user's skin. Thus, for example chafing is caused due to extra friction between the absorbent article and the skin of the user.

During frequent use of disposable absorbent articles, the skin can become irritated, appear red, and be sore to the touch. Creams, lotions, or ointments can be used to provide an artificial hydrophobic barrier on the skin and to treat skin conditions such as diaper rash. However, the use of such hydrophobic compositions has a negative impact on the absorbency performance of the articles.

It is an object of the present invention to provide an absorbent article having improved skin benefits, over the entire period of use.

SUMMARY OF THE INVENTION

One or more of the above objects may be achieved with an absorbent article in accordance with claim 1. Further embodiments are set out in the dependent claims, in the following description and in the drawings.

The absorbent article as disclosed herein has longitudinal side edges extending in a longitudinal direction and transverse front and rear end edges extending in a transverse direction. The absorbent article comprises a fluid permeable surface layer, a backsheet and an intermediate layer located between the fluid permeable surface layer and the backsheet. The surface layer has a wearer-facing portion facing the user during use. The surface layer is an air through bonded fibrous nonwoven surface layer that may have a basis weight of from 14 to 30 g/m² and a density of from 20 to 90 kg/m³. The intermediate layer may extend under from 70 to 100% of the wearer-facing portion of the surface layer. The intermediate layer and the surface layer may have a respective elongation at 10 N/50 mm, wherein the elongation at 10 N/50 mm of the intermediate layer is lower than the elongation at 10 N/50 mm of the surface layer. The elongation is measured according to the test method NWSP 110.4.RO (15). The elongation is measured in the machine direction of the material.

The intermediate layer may also cover from 50 to 100% of the wearer-facing portion of the surface layer.

The absorbent article may comprise wings or flaps provided with attachment means, such as adhesive. The wearer-facing portion of the surface layer means the portion of the surface layer facing the user during use and is not intended to include wings or flap as these are not intended to face the user during use.

The term "absorbent articles" refers to products that are placed against the skin of the wearer to absorb and contain body exudates, like urine, faeces and menstrual fluid. The disclosure mainly refers to disposable absorbent articles, which means articles that are not intended to be laundered or otherwise restored or reused as an absorbent article. Examples of disposable absorbent articles include feminine hygiene products such as sanitary napkins and panty liners, incontinence pads and diapers and the like.

The air through bonded fibrous nonwoven surface layer having a basis weight of from 14 to 30 g/m² and a density of from 20 to 90 kg/m³ has been found to provide the surface layer with surprisingly low friction values against the skin both under dry and wet conditions. A low friction between the wearer-facing surface layer and the skin decreases the risk for chafing of the skin against the napkin which otherwise may lead to skin irritation and itchiness.

The air through bonded fibrous nonwoven surface layer additionally provides the absorbent article with a rapid inlet with a reduced liquid spreading surface, keeping the skin dryer and reducing the wet friction.

Air through bonded fibrous nonwoven are known for use in absorbent articles as intermediate layers, such as acquisition layers, due to its bulky and airy structure. However, the material has been found by the present inventors to provide surprisingly low friction values when used as a surface layer in an absorbent article. However, the fact that the material has a low-density structure with relatively low amount of bonding points between the fibers gives a structure with lower integrity. Surface layer materials for absorbent articles are exerted to stretching and rubbing against the skin during use, to use a material with a lower integrity may risk the integrity of the material during use. To have a certain integrity is also important during the manufacturing of the absorbent articles and when combining the air through bonded fibrous nonwoven surface layer with an intermediate layer having a lower elongation than the air through bonded fibrous nonwoven, the air through bonded fibrous nonwoven surface layer integrity is increased.

The air through bonded fibrous nonwoven surface layer and the intermediate layer may be attached to each other. This may increase the integrity of the surface layer. The air through bonded fibrous nonwoven surface layer and the intermediate layer may be attached to each other by adhesive, by thermo welding, mechanical welding or a combination thereof.

The elongation of the intermediate layer may be at least 5% lower or at least 20% lower than the elongation of the surface layer, or at least 50% lower than the elongation of the surface layer. The elongation of the intermediate layer may be from 5% to 80% lower, or 20% to 80% lower than the elongation of the surface layer. This provides for an improved integrity for the air through bonded fibrous nonwoven and a low-friction surface layer for the absorbent article.

In the through-air bonding process, hot air is passed through the fibrous web to heat and melt polymer fibers. Molten polymer subsequently flows to the point of contact between any two fibers to produce a bond. The fibers in the nonwoven surface layer are thermoplastic polymeric fibers. One reason behind the surprisingly low friction of the material may be that the through-air bonding process enables a reduced number if binding points between the fibers.

The air through bonded fibrous nonwoven may comprise bicomponent fibers. At least 50%, or at least 80% of the fibers in the air through bonded fibrous nonwoven may be bicomponent fibers, such as from 50% to 95% of the fibers may be bicomponent fibers. Optionally all the fibers in the air through bonded fibrous nonwoven may be bicomponent fibers.

The bi-component fibers may be sheath-core bicomponent fibers, wherein the sheath may be of polyethylene or polypropylene. The core in the sheath-core bicomponent fibers may be of polyester. Such fibers have been found to provide nonwoven material with high resiliency and recovery. The bicomponent fibers may be sheath-core bicomponent fibers wherein the core is a polyester core and the sheath is a polyethylene sheath. Bicomponent fibers wherein the core is a polyester core and the sheath is a polyethylene sheath have been found to provide resilient structures with low friction and high drapability. A resilient structure gives the air through bonded fibrous nonwoven high bulk which improves the liquid absorption into the fabric.

The intermediate layer may be airlaid nonwoven, high loft nonwoven such as for example air-through bonded nonwoven or hydroentangled nonwoven. The intermediate layer may have a basis weight of from 30 to 120 gsm or 30 to 80 gsm, or 40 to 80 gsm.

The intermediate layer may be a laminate, such as a laminate of two or more nonwoven materials.

The fibers of the air through bonded nonwoven may have a coarseness of from 1.8 to 10 dTex, or 2 to 7 dTex. Such fibers may provide a reduced friction also when only a very small amount of moisture is present originating from for example perspiration.

The intermediate layer may cover from 80% to 100% of the wearer-facing portion of the surface layer, such as from 95% to 100% of the wearer-facing portion of the surface layer. If the absorbent article does not contain any wings, the intermediate layer may extend under from 85% to 100% of the total surface area of the surface layer.

The surface layer and the intermediate layer may be adhesively attached to each other, or attached to each other by thermo- or mechanical welding, such as for example ultra sonic welding or a combination thereof.

If the surface layer and the intermediate layer is adhesively attached to each other over an evenly spread adhesive area corresponding to 50% or more of the surface area of the intermediate layer. An adhesive layer may for example be provided by spraying or by slot coating.

If the surface layer and the intermediate layer is attached to each other by thermo- or mechanical welding, such as for example ultra sonic welding the laminated area may correspond to 10% or more, or 15% or more of the surface area of the intermediate layer, such as for example 10% to 50% of the surface area of the intermediate layer.

The surface layer may be attached to the backsheet along the longitudinal side edges and along the transverse end edges in a border attachment portion and wherein the intermediate layer extends between the surface layer and the backsheet in the border attachment portion.

The surface layer may be embossed with an embossing pattern. The embossing pattern may cover from 3% to 20% of the wearer-facing portion of the surface layer. This has been found to provide a soft and compliant surface sheet with a good visibility of the embossed elements.

The surface layer may be free from lotions and/or lubricating agents. As the surface layer in it-self has been found to provide the surface layer with surprisingly low friction values both under dry and wet conditions, lotions and lubricant agents may not be needed to decrease the friction between the nonwoven and the user's skin.

BRIEF DESCRIPTION OF THE DRAWINGS

The present invention will be further explained hereinafter by means of non-limiting examples and with reference to the appended drawings wherein.

DETAILED DESCRIPTION

Figure 1:
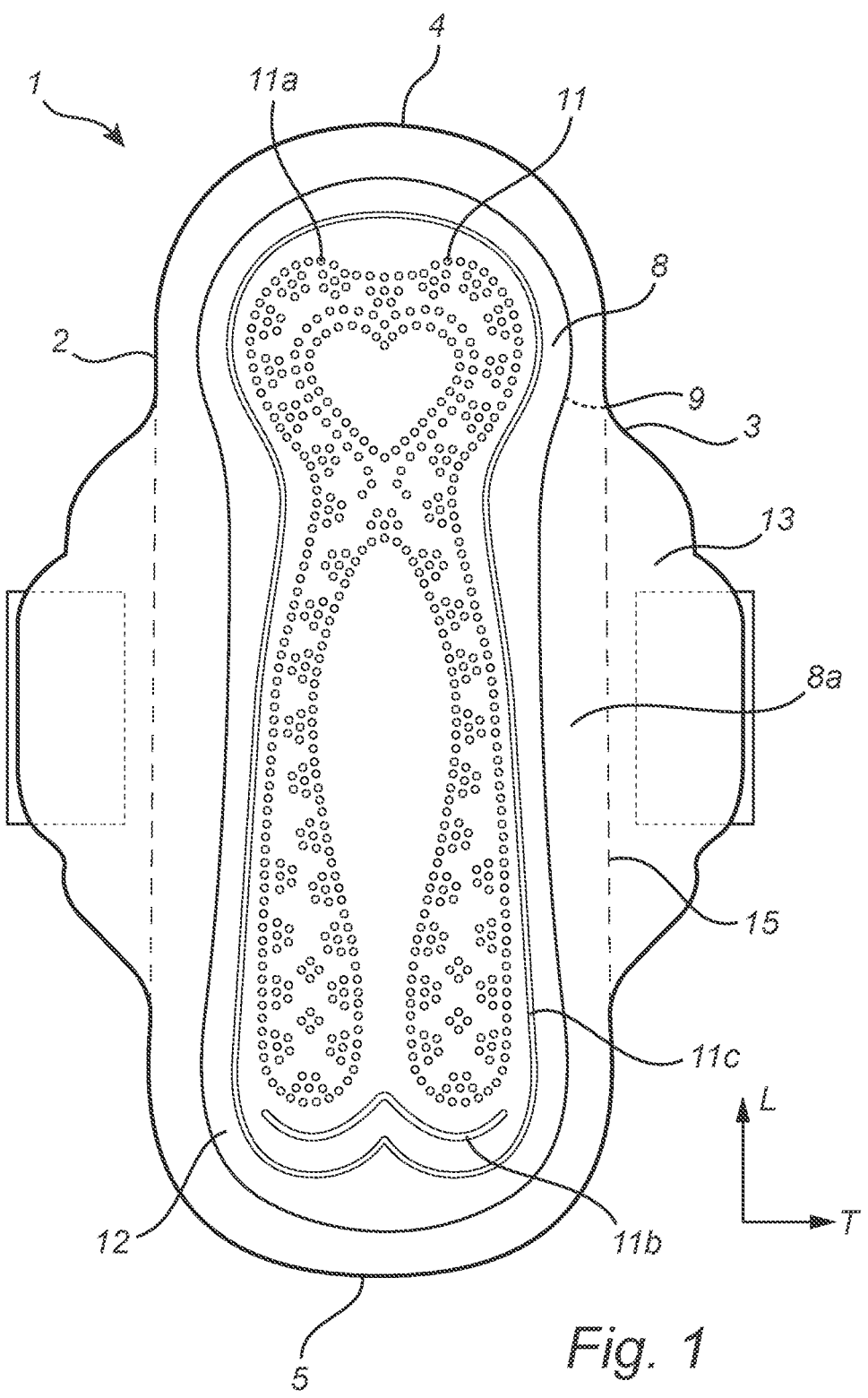
FIG. 1 shows a top plan view of a sanitary napkin as disclosed herein and as seen from a topsheet side.

The invention will be described more closely below by reference to an exemplary embodiment. The invention may however be embodied in many different forms and should not be construed as limited to the embodiments set forth in the drawings and the description thereto.

FIG. 1 is a top plan view of a sanitary article 1 having longitudinal side edges 2,3 extending in a longitudinal direction L and transverse front and rear end edges 4,5 extending in a transverse direction T. The sanitary article 1 comprising a fluid permeable surface layer 8 and a backsheet 9. The surface layer is an air through bonded fibrous nonwoven surface layer having a basis weight of from 14 to 30 $g/m^2$ and a density of from 20 to 90 $kg/m^3$. The nonwoven layer comprises bicomponent fibers and may constitute of from 50% or more, such as 80% to 100% or from 95% or more, of bicomponent fibers.

The bicomponent fibers may be sheath-core bicomponent fibers wherein the core is a polyester core and the sheath is a polyethylene sheath. Under the surface layer 8 the absorbent article 1 is provided with a fibrous intermediate layer 10 (see FIG. 2). The intermediate layer 10 extends under 100% of the wearer-facing portion 8a of the surface layer 8, the border of the wearer-facing portion being indicated with a dotted line 15. The intermediate layer 10 and the surface layer 8 have a respective elongation at 10 N/50 mm, wherein the elongation of the intermediate layer 10 is lower than the elongation of the surface layer 8.

The fluid permeable surface layer 8 comprises an embossed pattern 11. The embossed pattern 11 comprises individual embossed elements 11a in the form of dots forming a pattern covering from 3% to 20% of the wearer-facing portion of the surface layer 8. At a rear end 12 of the absorbent article 1, the surface layer 8 is provided with an embossed wing-shaped continuous line 11b and a continuous embossed line extends along a contour of the absorbent article 1 framing the embossed pattern 11.

The absorbent article 1 in FIG. 1 is a sanitary napkin provided with a pair of lateral wings 13 extending outward from the transversely opposite side edges 2,3 of the napkin. The wings are provided with attachment means, such as with an adhesive, on their garment facing surface so that the wings 13 can be folded back under the undergarment and attached to the undergarment. In this way, the wings 13 serve to keep the napkin 1 properly positioned in the undergarment.

Figure 2:
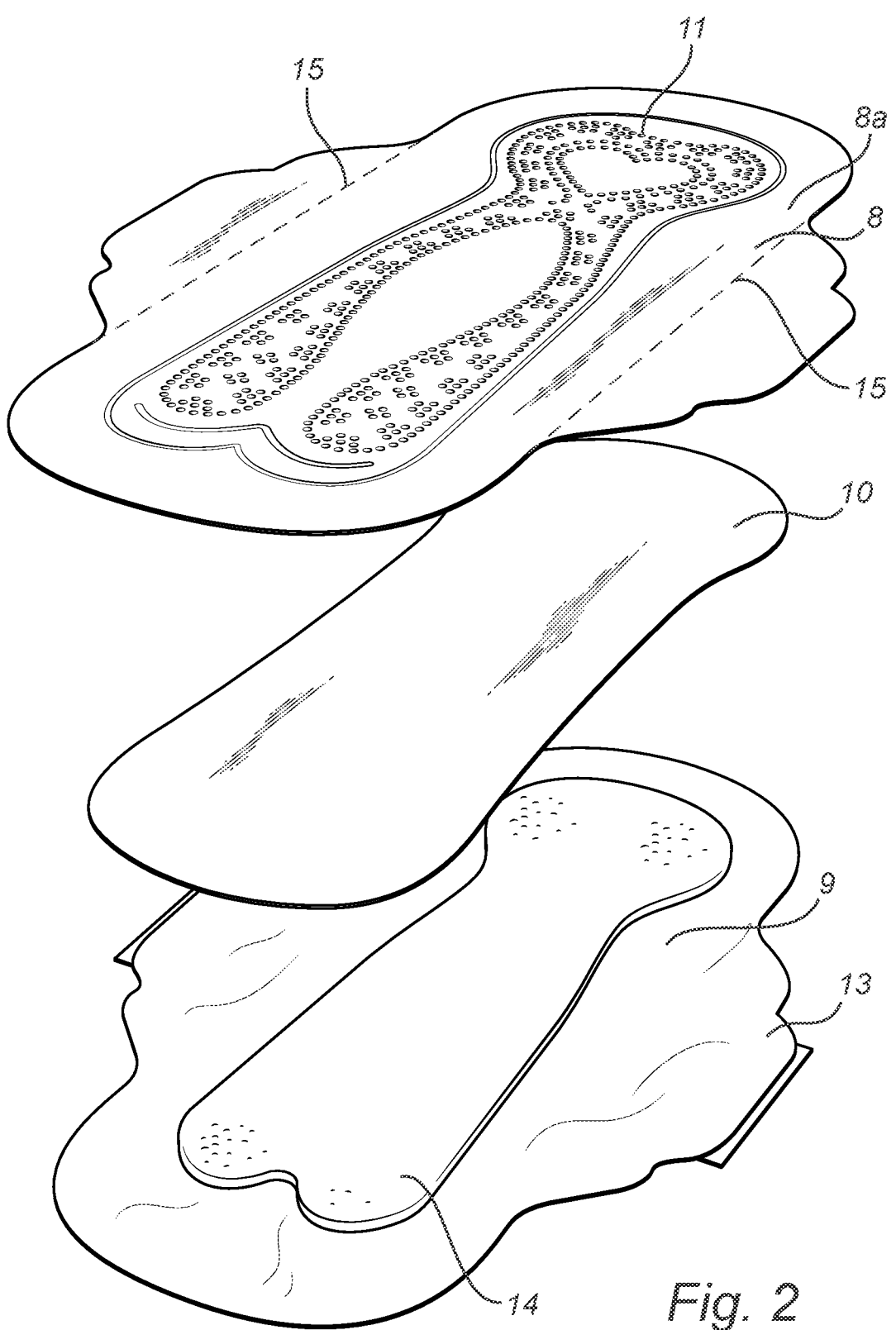
FIG. 2 shows an exploded perspective view the sanitary napkin of FIG. 1.

FIG. 2 is an exploded view of the sanitary napkin 1 shown in FIG. 2 and illustrates the sanitary napkin 1 with the individual layers of the sanitary napkin 1 separated. The sanitary napkin 1 comprises the fluid permeable surface layer 8 and the backsheet 9. The intermediate fibrous layer 10 is located between the surface layer 8 and the backsheet 9 and is in direct contact with the surface layer 8. The intermediate layer 10 and the surface layer 8 has a respective elongation at 10 N/50 mm. The elongation at 10 N/50 mm of the intermediate layer 10 is lower than the elongation at 10 N/50 mm of the surface layer 8. In this figure the intermediate layer is provided under about 100% of the total surface area of the wearer-facing portion 8a of the surface layer 8 and is adhesively attached to the surface layer 8. An absorbent core 14 is arranged between the intermediate layer 10 and the backsheet 9.

The backsheet may be a breathable or non-breathable plastic film. The plastic film may be of polyolefine. The backsheet may be a laminate of a breathable or non-breathable plastic film and a nonwoven material.

The absorbent core may be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent structure. It is also common to have absorbent structures comprising layers of different material with different properties with respect to liquid acquisition capacity, liquid distribution capacity and storage capacity. This is well-known to the person skilled in the art and does therefore not have to be described in detail. The thin absorbent bodies, which are common in today's sanitary articles, often comprise a compressed mixed or layered structure of cellulosic fluff pulp and superabsorbent. The size and absorbent capacity of the absorbent structure may be varied to be suited for different uses such as sanitary articles, pantyliners, adult incontinence pads and diapers, baby diapers, pant diapers, etc.

The intermediate layer may be a nonwoven layer, for example a laminate of two or more nonwoven materials. The intermediate layer may be composed of for example airlaid nonwoven, spunlace nonwoven, carded air-through bonded nonwoven, high loft nonwoven or foam materials. The nonwoven material may be hydrophilic. A hydrophilic material may be obtained by adding a surfactant. An air laid nonwoven can be produced with fluff, wood pulp, and here the fluff fibres are dispersed into a fast-moving air stream and condensed onto a moving screen by means of pressure and vacuum. The web can be bonded with resin and/or thermal plastic resin dispersed within the pulp. The web can be thermobonded (by heat), latex bonded (with adhesive) or multibonded (a combination of thermo and latex bonding) or mechanically bonded (high compression and temperature, bonding by hydrogen). The grammage of the airlaid nonwoven can suitably be from 50 to 100 gsm. The grammage of the carded air-through bonded nonwoven can suitably be from 40 to 100 gsm.

High loft is a nonwoven material and may be substantially free from absorbing fibres and superabsorbent material. The high loft nonwoven material may comprise thermoplastic polymer fibres, and may be selected from but not limited to, polyesters, polyamides and polyolefins such as polyethylenes (PE) and polypropylenes (PP), and may be a mixture of any of these. The "high loft" refers to low density bulky fabrics, as compared to flat, paper-like fabrics. High loft webs are characterized by a relatively low density. This means that there is a relatively high amount of void space between the fibres. The high loft nonwoven fibrous layer of the invention may typically have a density below 0.200 g/cc (200 kg/m³), in particular ranging from 0.015 g/cc to 0.150 g/cc (15 kg/m³ to 150 kg/m³), in particular from 0.030 g/cc to 0.100 g/cc (30 to 100 kg/m³), for example 0.065 g/cc (65 kg/m³). The average density can be calculated by dividing the basis weight of the high loft layer by its thickness measured at a pressure of 0.5 kPa. Normally the thickness of high loft materials is more than about 0.5 mm, such as more than 1 mm or suitably 1.5-2.0 mm, and the solid content is low, usually less than 15% by volume. The high loft nonwoven layer may advantageously be a spunmelt nonwoven. Spunmelt is a generic term describing the manufacturing of nonwoven webs directly from thermoplastic polymers The high loft nonwoven layer may in particular have a thickness ranging from 0.30 mm to 2.00 mm, for example 1.0 mm as measured at a pressure of 0.5 kPa.

The intermediate layer may comprise or constitute of a spunlace nonwoven material. A spunlace nonwoven product is derived from a process of entangling a web of loose fibres through multiple rows of jets of water at high pressure; this process entangles the fabrics and interlinks the fibres.

The raw material for the acquisition sheet can be polypropylene (PP), polyethylene (PE) polyester (PET), polyamide (PA), cellulosic fibres or a combination of these and different weights and compositions are possible, such as viscose, polyester, cotton, nylon and microfibre. Thus, if a combination of different fibres is used, this can be a mixture of fibres from different polymers, although each fibre can also include different polymers (e.g. PP/PE bi-component fibres or PP/PE copolymers). The grammage of the spunlace nonwoven material can be typically from 40-90 gsm.

The surface layer and the intermediate layer may be adhesively attached to each other.

This may increase the integrity of the surface layer. When combining the air-through-bonded fibrous nonwoven surface layer with an intermediate layer having a lower elongation than the air-through-bonded fibrous nonwoven, the air-through-bonded fibrous nonwoven surface layer integrity is increased. Both during use of the absorbent product as well as during manufacturing it is advantageous that a structure(s) has a sufficient integrity.

Both during use of the absorbent product as well as during manufacturing it is advantageous that a structure(s) has a sufficient integrity.

It is also possible to laminate the liquid surface material together with the intermediate layer through thermo- and or mechanical welding, for example by ultrasonic welding.

Figure 3:
FIG. 3 shows friction measurement result on surface materials

In FIG. 3 shows the friction curves for test sample, CEx 1 and CEx 2. In FIG. 4 is the number of runs on the x-axis and the friction force in gmf on the y-axis. A friction curve comprises a first slope having a positive coefficient illustrating increase in the friction values, a plateau, and a second slope having a negative coefficient illustrating decrease in friction values. At the plateau, the friction values are substantially constant over the extension of the plateau. Small variations at the plateau as well as along the slopes are possible between individual values, but with a positive coefficient is meant that all individual values in the first slope together creates a positive coefficient, as well as all individual values in the second slope together creates a negative coefficient, as well as all individual values in the plateau together creates a plateau. Lower friction values render the absorbent article more skin friendly and skin problems arising with the use of the absorbent article can be reduced. For some materials a clear peak can be seen in a curve of friction values before the second slope creating a negative coefficient. Such a peak is caused by clinging, which may occur when only a small amount of moisture is present. The result shows that the test sample, the airthrough-bonded nonwoven surface material has a lower mean friction plateau value (gmf) than CEx 1 and CEx 2.

Density Measurement

The density is calculated by dividing the basis weight of the fibrous nonwoven surface layer by its thickness measured at a pressure of 0.5 kPa. The thickness is determined by means of a measuring foot with affixed load of 0.5 kPa having a foot area of 50×50 mm$^2$. The thickness is read off at the digital thickness gauge/tester after 10 seconds when the measuring foot has touched the surface of the sample.

Elongation Measurement

Elongation is measured according to the EDANA/INDA standard procedure NWSP 110.4.RO (15), method option B (dry testing). The test is performed on a conventional tensile tester (constant rate of extension), available from the Instron or Lloyd corporations. Samples having the width 50 mm and the length of at least 200 mm are punched out from the material. The machine direction (MD) is in the same direction as the length of the sample. The material is extended in the machine direction in a rate of 100 mm/min. When a load of 10 Newtons has been obtained, the extension of the material is read. Five individual samples are tested, and the mean value is reported, which is the value of the elongation at 10N/50 mm.

Initial Spreading Measurement

The initial spreading for a surface layer material according to the present disclosure was compared with a conventional spunbond surface layer 20 g/m$_2$. The method used was the FLOW method and a sanitary napkin according to the present invention and comprising an air through bonded nonwoven 20 g/m$_2$ from TWE, loft 286, as surface layer and combined with an intermediate layer in the form of an airlaid nonwoven material 65-70 g/m$_2$, was compared with a sanitary napkin comprising a surface layer of a spunbonded nonwoven material combined with an intermediate layer in the form of an airlaid nonwoven material 65-70 g/m$_2$. Each of the test articles included a pulp core and a liquid impermeable polyolefin plastic film backsheet. The test samples are conditioned in 24±4 h at 50±10% r.h. and 23±1° C. The number of samples for each test type is 6. The samples are placed on a Plexiglas table with an angle of 25°.

According to the FLOW method, 5 ml of test liquid, synthetic menstrual fluid, is added to the sanitary napkins provided with the respective materials as surface layers, the test liquid is added in a dose 1, 2 and 3 with an interval of 15 seconds and with a flow speed of 20/min. After this the spreading length (mm) of the liquid was measured for each of the materials and is shown in the Table 1 below. When the fluid has been added, the longest distance the fluid has run on top of the surface material is measured.

TABLE 1

| | Test sample, Air through bonded nonwoven (TWE) | CEx 2, Spunbond nonwoven (Union) |
|---|---|---|
| Dose 1 | 51 mm | 71 mm |
| Dose 2 | 74 mm | 88 mm |
| Dose 3 | 94 mm | 113 mm |

As illustrated in table 1, the spreading length of the liquid and thereby the wetted surface area is lower for the surface material according to the present invention. Details for the materials tested is shown below in Table 2.

Friction Measurement

A fluid permeable surface layer according to claim 1 has a wet friction reducing property. Friction occurring between a nonwoven material and the skin of the user is different in the presence of liquid/moisture than when no liquid/moisture is present. Even a very small amount of moisture present originating from perspiration, sweat or other body fluids has an impact on the friction forces occurred between the nonwoven material and the skin of the user. It has therefore been discovered that it is important to carefully choose the nonwoven characteristics, so that the nonwoven is able to minimize the mechanical discomfort during the overall use of the product. The method used is called Stick and slip measurement method for measuring the wet friction and the method measures the static friction, sns value (stick and slip value) in gram force, gmf, between a material and the human skin. Repeatedly runs are made using the same material strip. First the sns value for the dry state (dry material and skin) is measured followed by wet state at different liquid levels (from completely wetted material, to moist and to almost dry) until the sns value is back to the skin-material interaction level measured in the first dry run, which mean that the material is dry again. The method is thus called a repeated stick and slip method or sns dry-wet-dry. The stick and slip value is defined as the point on the force curve (gmf) where the material starts gliding over the arm. The sns values from all single force curves are then put together in a new graph, sns values as a function of number of runs.

Three different nonwoven materials were tested and compared in terms of dry friction and wet friction. The test material is an air-through-bonded nonwoven according to the present disclosure comprising bicomponent fibers of core-sheath type with a polyester core and a polyethylene sheath. The first Comparative Example is a spunbond nonwoven with polypropylene fibers and the second Comparative Example is spunbond nonwoven with polypropylene fibers. Table 2 below provides specifications of the materials tested.

TABLE 2

| | Material Type | Supplier | Material no | Basis weight (gsm) |
|---|---|---|---|---|
| Test sample | Air-though bonded nw | TWE | 255272 | 20 |
| CEx 1 | Spunbond nonwoven | Texbond | 2436701 | 18 |
| CEx 2 | Spunbond nonwoven | Union | 272119 | 18 |

In table 3 below shows result of the mean friction plateau values measured in gmf. By gmf is meant gram-force and one gram-force is 9.80665 mN and the result shows that the test sample, the air-through-bonded nonwoven surface material has a lower mean friction plateau value (gmf) than CEx 1 and CEx 2.

TABLE 3

| Material | Mean friction plateau value, (gmf) |
|---|---|
| Test sample | 300 |
| CEx 1 | 480 |
| CEx 2 | 420 |

Also in FIG. 3 shows the friction curves for test sample, CEx 1 and CEx 2. In FIG. 4 is the number of runs on the x-axis and the friction force in gmf on the y-axis and the result shows that the friction curve for the test sample, the air-through-bonded nonwoven surface material, has a lower mean friction plateau value (gmf) than the friction curves for CEx 1 and CEx.

The invention claimed is:

1. An absorbent article having longitudinal side edges extending in a longitudinal direction and transverse end edges, and comprising:

a fluid permeable uppermost surface layer, a backsheet and an intermediate layer being located between said surface layer and said backsheet, the fluid permeable surface layer having a wearer-facing portion facing the user during use of said article, wherein said surface layer is a single layer of an air through bonded fibrous nonwoven comprising synthetic fibers and having a basis weight of from 14 to 30 g/m$^2$ and a density of from 20 to 90 kg/m$^3$, wherein said intermediate layer is provided under from 70% to 100% of a total surface area of the wearer-facing portion of the surface layer, wherein each of said intermediate layer and said surface layer has a respective elongation at 10 N/50 mm, and wherein said elongation of said intermediate layer is lower than said elongation of said surface layer, wherein an entirety of where the surface layer abuts the intermediate layer is essentially on a same plane.

2. The absorbent article according to claim 1, wherein the surface layer is laminated to the intermediate layer and the lamination is made by adhesive, thermo or mechanical welding, or a combination thereof.

3. The absorbent article according to claim 1, wherein said surface layer of air through bonded fibrous nonwoven comprises bicomponent fibers.

4. The absorbent article according to claim 3, wherein said bi-component fibers are sheath-core bicomponent fibers, wherein said sheath is a polyethylene sheath.

5. The absorbent article according to claim 4, wherein said core is a polyester core.

6. The absorbent article according to claim 1, wherein said elongation of said intermediate layer is at least 5% or at least 20% lower than said elongation of said surface layer.

7. The absorbent article according claim 1, wherein said intermediate layer has a basis weight higher than the basis weight of the surface layer.

8. The absorbent article according to claim 1, wherein said intermediate layer is a nonwoven material.

9. The absorbent article according to claim 1, wherein said fibers of said air through bonded nonwoven have a coarseness of from 1.8 to 10 dTex.

10. The absorbent article according to claim 1, wherein said intermediate layer extends under from 85% to 100% of said surface layer.

11. The absorbent article according to claim 1, wherein said surface layer and said intermediate layer are adhesively attached to each other.

12. The absorbent article according to claim 1, wherein said backsheet has a garment facing side and wherein an adhesive is arranged on said garment facing side.

13. The absorbent article according to claim 1, wherein at least said surface layer is embossed with an embossing pattern.

14. The absorbent article according to claim 1, wherein the surface layer is laminated to the intermediate layer and the lamination is made by ultra-sonic welding.

15. An absorbent article having longitudinal side edges extending in a longitudinal direction and transverse end edges, and comprising:

a fluid permeable surface layer, a backsheet and an intermediate layer being located between said surface layer and said backsheet, the fluid permeable surface layer having a wearer-facing portion facing the user during use of said article, wherein said surface layer is an air through bonded fibrous nonwoven surface layer comprising synthetic fibers and having a basis weight of from 14 to 30 g/m$^2$ and a density of from 20 to 90 kg/m$^3$, wherein said intermediate layer is provided under from 70% to 100% of a total surface area of the wearer-facing portion of the surface layer, wherein each of said intermediate layer and said surface layer has a respective elongation at 10 N/50 mm, and wherein said elongation of said intermediate layer is lower than said elongation of said surface layer, wherein said surface layer is attached to said backsheet along said longitudinal side edges and along said transverse end edges in a border attachment portion and wherein said intermediate layer extends between said surface layer and said backsheet in said border attachment portion.

16. An absorbent article having longitudinal side edges extending in a longitudinal direction and transverse end edges, and comprising:

a fluid permeable uppermost surface layer, a backsheet, an intermediate layer being located between said surface layer and said backsheet, and an absorbent core being located between said intermediate layer and said backsheet, the fluid permeable surface layer having a wearer-facing portion facing the user during use of said article, wherein said surface layer is a single layer of an air through bonded fibrous nonwoven comprising synthetic fibers and having a basis weight of from 14 to 30 g/m$^2$ and a density of from 20 to 90 kg/m$^3$, wherein said intermediate layer is provided under from 70% to 100% of a total surface area of the wearer-facing portion of the surface layer, wherein each of said intermediate layer and said surface layer has a respective elongation at 10 N/50 mm, and wherein said elongation of said intermediate layer is lower than said elongation of said surface layer, wherein, in an area overlapping the absorbent core, an entirety of where the surface layer abuts the intermediate layer is essentially on a same plane.

* * * * *